United States Patent [19]
Kawasaki

[11] Patent Number: 5,853,002
[45] Date of Patent: Dec. 29, 1998

[54] PEDIATRIC NEBULIZER ENHANCER

[76] Inventor: Mary Kelly Kawasaki, 94-1045 Ohilau Pl., Waipahu, Hi. 96797

[21] Appl. No.: 818,296

[22] Filed: Mar. 14, 1997

[51] Int. Cl.⁶ ............................................. A61M 16/00
[52] U.S. Cl. ............................. 128/200.14; 128/200.21; 128/203.12; 128/204.18
[58] Field of Search ................... 128/200.14, 200.21, 128/200.11, 200.24, 203.28, 204.18, 200.22, 203.12

[56] References Cited

U.S. PATENT DOCUMENTS

| | | | |
|---|---|---|---|
| 4,231,973 | 11/1980 | Young et al. | 128/200.11 |
| 4,253,468 | 3/1981 | Lehmbeck | 128/200.21 |
| 4,606,328 | 8/1986 | Thoman . | |
| 4,823,784 | 4/1989 | Bordoni et al. | 128/200.21 |
| 5,020,530 | 6/1991 | Miller | 128/203.28 |
| 5,690,096 | 11/1997 | Burch | 128/200.24 |

*Primary Examiner*—John G. Weiss
*Assistant Examiner*—V. Srivastava
*Attorney, Agent, or Firm*—Michael I. Kroll

[57] ABSTRACT

A pediatric nebulizer enhancer (10) comprising a T-fitting (12). A structure (14) is for mounting a first end (16) of the T-fitting (12) to a dome cover (18) on a dome (20), which holds medication and saline, that is connected to an end of a tubing (21) from an oxygen outlet. A plug (22) is for sealing off a second end (24) of the T-fitting (12). A facility (26) on a third end (28) of the T-fitting (12) is for spraying a medicated mist (29) directly into a face (30) of a child (32). The child (32) can focus onto the spraying facility (26) without any fear, by being attracted to the spraying facility (26).

27 Claims, 3 Drawing Sheets

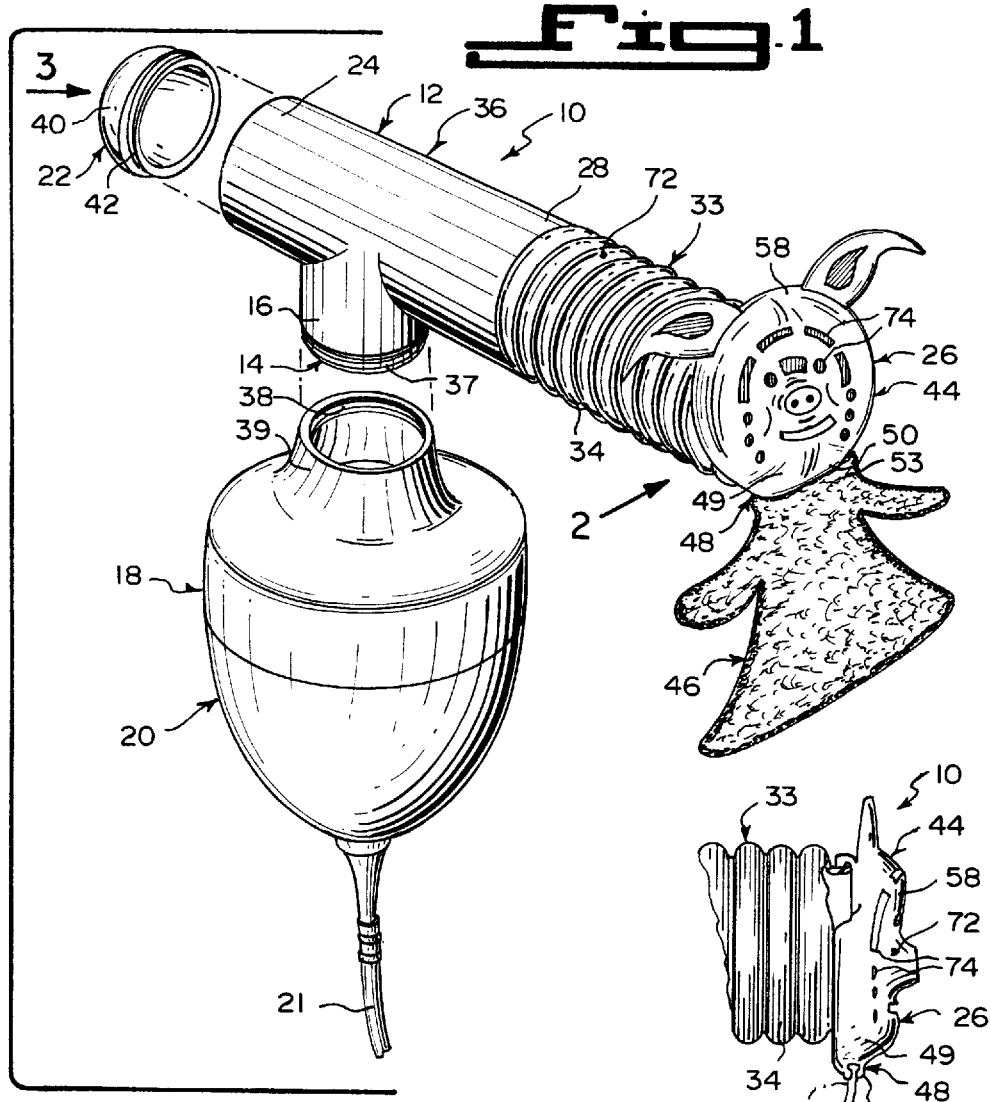
Fig.1
Fig.2
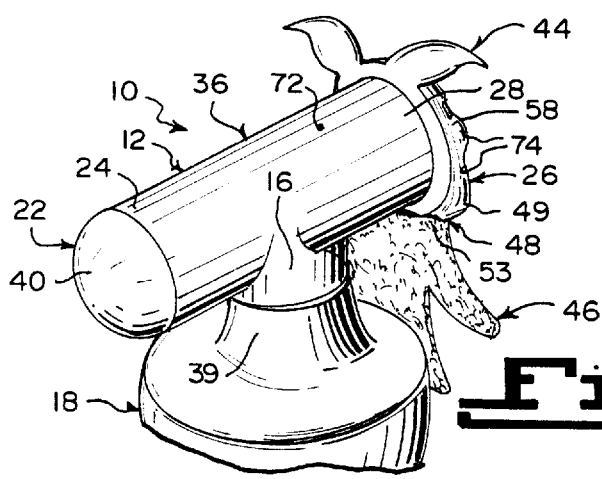
Fig.3

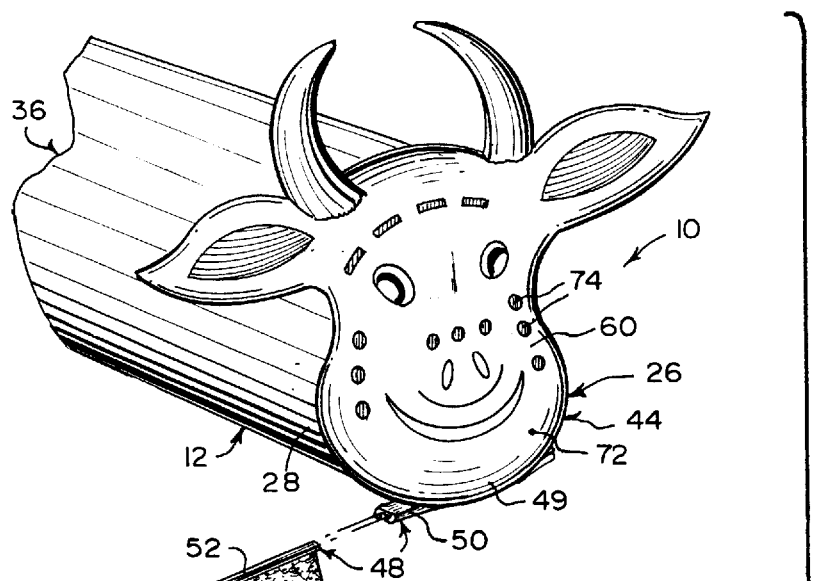
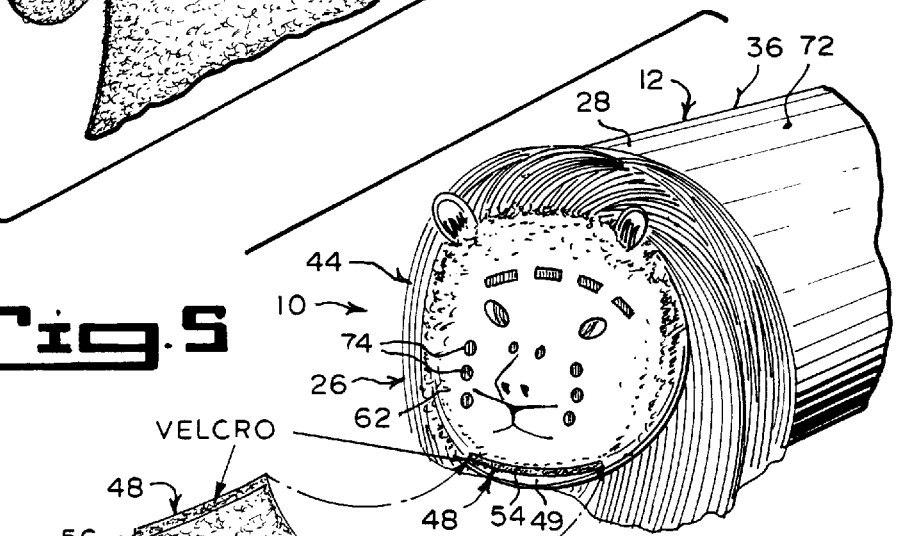

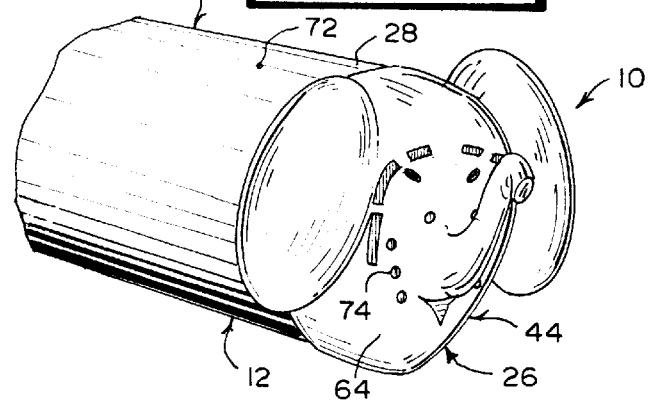
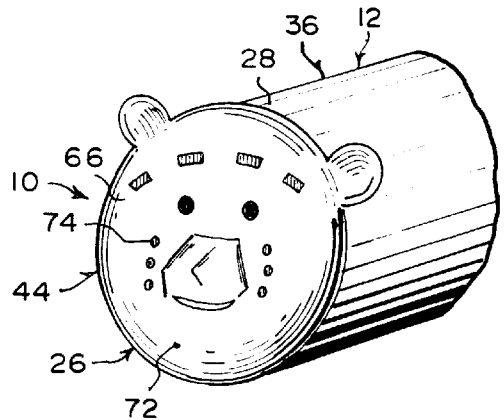
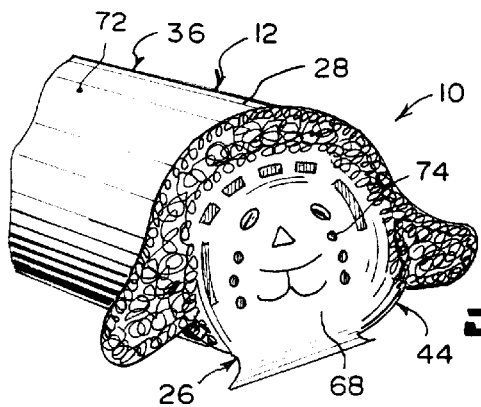
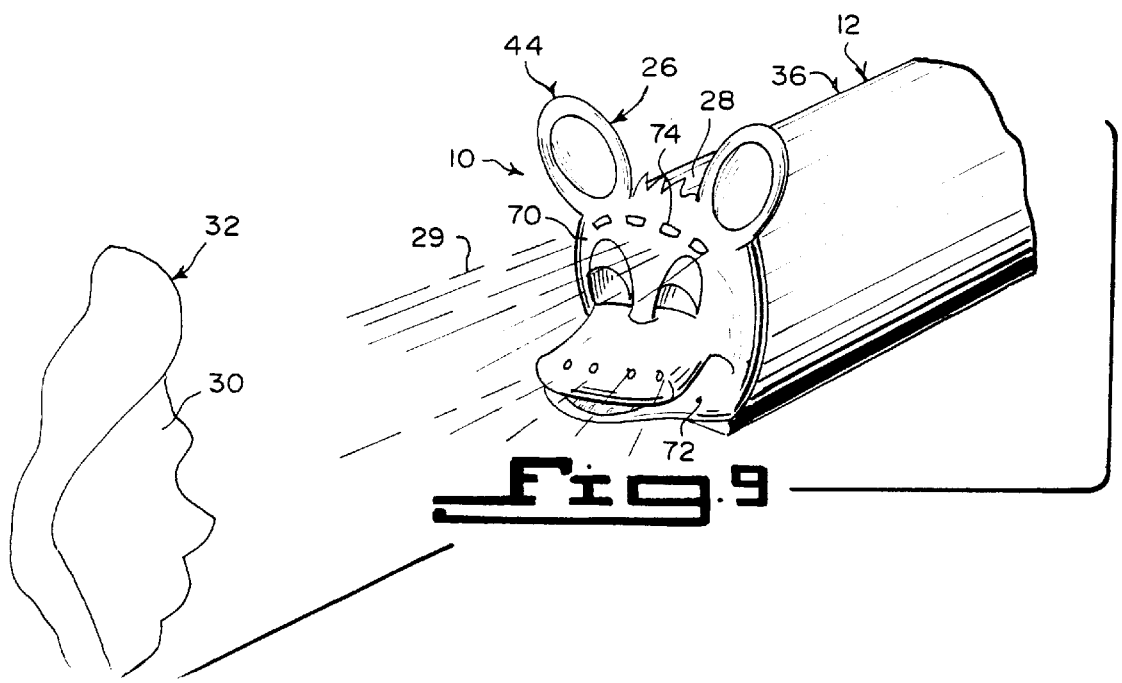

PEDIATRIC NEBULIZER ENHANCER

BACKGROUND OF THE INVENTION

1. Field of the Invention

Asthma is the most common of the chronic lung diseases diagnosed in children and accounts for a large percentage of emergency department/hospital admissions. Recently, the use of continuous and intermittent administration of Beta-adrenegric agents has been found to be a safe and effective method of therapy for the pediatric patient experiencing severe asthma. An understanding of equipment, monitoring parameters, and nursing implications can help prepare pediatric and emergency room nurses to provide care for children receiving continuous and intermittent nebulization. An urban hospital in the northeastern United States organized a multidisciplinary team to investigate the use of continuous nebulization of Beta 2 agonists in the care of the pediatric patient experiencing an acute asthma episode.

The instant invention relates generally to nebulizers and more specifically it relates to a pediatric nebulizer enhancer. The pediatric nebulizer enhancer will allow for a greater accuracy for administering nebulized treatments to children with special needs, such as asthma.

2. Description of the Prior Art

Numerous nebulizers have been provided in prior art that are adapted to spray medicated liquid doses, so that the doses can be breathed into the lungs of patients, for the treatment of asthma and other respiratory diseases. While these units may be suitable for the particular purpose to which they address, they would not be as suitable for the purposes of the present invention as heretofore described.

SUMMARY OF THE INVENTION

A primary object of the present invention is to provide a pediatric nebulizer enhancer that will overcome the shortcomings of the prior art devices.

Another object is to provide a pediatric nebulizer enhancer that will allow for a greater accuracy for administering a nebulized treatment of a sprayed medicated mist into the face of a child with a special need, such as asthma.

An additional object is to provide a pediatric nebulizer enhancer in which a perforated animal face on an end of the enhancer will serve to distract the child, so that the sprayed medicated mist can be directed into the face of the child to inhale the sprayed medicated mist.

A further object is to provide a pediatric nebulizer enhancer that is simple and easy to use.

A still further object is to provide a pediatric nebulizer enhancer that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 1 is a partly exploded front perspective view of a first embodiment of the instant invention, showing a perforated pig face.

FIG. 2 is a side view taken in the direction of arrow 2 in FIG. 1, with parts broken away and the cloth body shown in phantom.

FIG. 3 is an assembled rear perspective view taken in the direction of arrow 3 in FIG. 1, with parts broken away and the flexible conduit removed therefrom.

FIG. 4 is a front perspective view of a second embodiment of the instant invention, showing a perforated cow face with parts broken away and the cloth body exploded therefrom.

FIG. 5 is a front perspective view of a third embodiment of the of the instant invention, showing a perforated lion face with parts broken away and the cloth body exploded therefrom.

FIG. 6 is a front perspective view of a fourth embodiment of the instant invention with parts broken away, showing a perforated elephant face.

FIG. 7 is a front perspective view of the fourth embodiment with parts broken away, showing a perforated bear face.

FIG. 8 is a front perspective view of the fourth embodiment with parts broken away, showing a perforated lamb face.

FIG. 9 is a front perspective view of the fourth embodiment with parts broken away, showing a perforated dog face spraying a medicated mist into a face of a child.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 1 through 9 illustrate a pediatric nebulizer enhancer 10 comprising a T-fitting 12. A structure 14 is for mounting a first end 16 the T-fitting 12 to a dome cover 18 on a dome 20, which holds medication and saline, that is connected to an end of a tubing 21 from an oxygen outlet (not shown).

A plug 22 is for sealing off a second end 24 of the T-fitting 12. A facility 26 on a third end 28 of the T-fitting 12 is for spraying a medicated mist 29 directly into a face 30 of a child 32. The child 32 can focus onto the spraying facility 26 without any fear, by being attracted to the spraying facility 26.

An elongate flexible conduit 33, as shown in FIGS. 1 and 2, can be attached between the third end 28 of the T-fitting 12 and the spraying facility 26, so as to put the child 32 further away from a noise produced at the dome 20. The elongate flexible conduit 33 is a piece of corrugated tubing 34. The T-fitting 12 is a hollow cylindrical housing 36. The mounting structure 14, as best seen in FIG. 1, is external threads 37 formed on the first end 16 of the T-fitting 12, so as to engage with internal threads 38 on a top neck 39 of the dome cover 18.

The plug 22 is a dome shaped cap 40 having a reduced diameter externally threaded collar 42 thereon, whereby the collar 42 threads into the second end 24 of the T-fitting 12. The spraying facility 26 is a perforated animal face 44.

The pediatric nebulizer enhancer 10 can further include a flat cloth body 46, as shown in FIGS. 1 through 5. An assembly 48 is for attaching the flat cloth body 46 to a bottom portion 49 of the perforated animal face 44.

The attaching assembly 48, as best seen in FIG. 4, consists of a track 50 on the bottom portion 49 of the perforated animal face 44. A rail 52 is affixed onto a neck segment 53 of the flat cloth body 46. The rail 52 can be inserted into the track 50, to hold the flat cloth body 46 under the perforated animal face 44.

The attaching assembly 48, as best seen in FIG. 5, comprises a first VELCRO strip 54 affixed onto the bottom portion 49 of the perforated animal face 44. A second VELCRO strip 56 is affixed onto the neck segment 53 of the flat cloth body 46. The second VELCRO strip 56 can mate with the first VELCRO strip 54, to hold the flat cloth body 46 under the perforated animal face 44.

The perforated animal face 44 can be of a pig 58, as shown in FIGS. 1, 2 and 3. The perforated animal face 44 can be of a cow 60, as shown in FIG. 4. The perforated animal face 44 can be of a lion 62, as shown in FIG. 5. The perforated animal face 44 can be of an elephant 64, as shown in FIG. 6. The perforated animal face 44 can be of a bear 66, as shown in FIG. 7. The perforated animal face 44 can be of a lamb 68, as shown in FIG. 8. The perforated animal face 44 can be of a dog 70, as shown in FIG. 9.

Other types of animal faces can also be utilized, such as a bird, a cat, a monkey, different human faces, a clown, etc. The enhancer 10 can be manufactured in all types of durable materials, including plastic 72. The perforated animal face 44 can have a plurality of apertures 74 of different sizes and shapes, to direct the medicated mist 29 towards the face 30 of the child 32.

LIST OF REFERENCE NUMBERS 10 pediatric nebulizer enhancer
12 T-fitting of 10
14 mounting structure of 10
16 first end of 12
18 dome cover on 20
20 dome connected to 21
21 tubing
22 plug of 10
24 second end of 12
26 spraying facility of 10
28 third end of 12
29 medicated mist
30 face of 32
32 child
33 elongate flexible conduit of 10
34 piece of corrugated tubing for 33
36 hollow cylindrical housing for 12
37 external threads on 16 for 14
38 internal threads on 39
39 top neck of 18
40 dome shaped cap for 22
42 externally threaded collar on 40
44 perforated animal face for 26
46 flat cloth body of 10
48 attaching assembly for 46
49 bottom portion of 44
50 track of 48 on 49
52 rail of 48 on 53
53 neck segment of 46
54 first VELCRO strip of 48 on 49
56 second VELCRO strip of 48 on 53
58 pig face for 44
60 cow face for 44
62 lion face for 44
64 elephant face for 44
66 bear face for 44
68 lamb face for 44
70 dog face for 44
72 plastic for 10
74 aperture in 44

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A pediatric nebulizer enhancer comprising:
    a) a T-fitting;
    b) means for mounting a first end of said T-fitting to a dome cover on a dome, which holds medication and saline, that is connected to an end of a tubing from an oxygen outlet;
    c) a plug to seal off a second end of said T-fitting;
    d) means on a third end of said T-fitting for spraying a medicated mist directly into a face of a child, so that the child can focus onto said spraying means without any fear, by being attracted to said spraying means, wherein said spraying means is a perforated animal face;
    e) a flat cloth body; and
    f) means for attaching said flat cloth body to a bottom portion of said perforated animal face.

2. A pediatric nebulizer enhancer as recited in claim 1, further including an elongate flexible conduit attached between the third end of said T-fitting and said spraying means, so as to put the child further away from a noise produced at the dome.

3. A pediatric nebulizer enhancer as recited in claim 2, wherein said elongate flexible conduit is a piece of corrugated tubing.

4. A pediatric nebulizer enhancer as recited in claim 1, wherein said T-fitting is a hollow cylindrical housing.

5. A pediatric nebulizer enhancer as recited in claim 1, wherein said mounting means is external threads formed on the first end of said T-fitting, so as to engage with internal threads on a top neck of the dome cover.

6. A pediatric nebulizer enhancer as recited in claim 1, wherein said plug is a dome shaped cap having a reduced diameter externally threaded collar thereon, whereby said collar threads into the second end of said T-fitting.

7. A pediatric nebulizer enhancer as recited in claim 1, wherein said attaching means, further includes:
    a) a track on the bottom portion of said perforated animal face; and
    b) a rail affixed onto a neck segment of said flat cloth body, whereby said rail can be inserted into said track to hold said flat cloth body under said perforated animal face.

8. A pediatric nebulizer enhancer as recited in claim 1, wherein said attaching means, further includes:
   a) a first VELCRO strip affixed onto the bottom portion of said perforated animal face; and
   b) a second VELCRO strip affixed onto a neck segment of said flat cloth body, whereby said second VELCRO strip can mate with said first VELCRO strip to hold said flat cloth body under said perforated animal face.

9. A pediatric nebulizer enhancer as recited in claim 1, wherein said perforated animal face is of a pig.

10. A pediatric nebulizer enhancer as recited in claim 1, wherein said perforated animal face is of a cow.

11. A pediatric nebulizer enhancer as recited in claim 1, wherein said perforated animal face is of a lion.

12. A pediatric nebulizer enhancer as recited in claim 1, wherein said perforated animal face is of an elephant.

13. A pediatric nebulizer enhancer as recited in claim 1 wherein said perforated animal face is of a bear.

14. A pediatric nebulizer enhancer as recited in claim 1, wherein said perforated animal face is of a lamb.

15. A pediatric nebulizer enhancer as recited in claim 1, wherein said perforated animal face is of a dog.

16. A pediatric nebulizer enhancer as recited in claim 3, wherein said T-fitting is a hollow cylindrical housing.

17. A pediatric nebulizer enhancer as recited in claim 16, wherein said mounting means is external threads formed on the first end of said T-fitting, so as to engage with internal threads on a top neck of the dome cover.

18. A pediatric nebulizer enhancer as recited in claim 17, wherein said plug is a dome shaped cap having a reduced diameter externally threaded collar thereon, whereby said collar threads into the second end of said T-fitting.

19. A pediatric nebulizer enhancer as recited in claim 18, wherein said attaching means, further includes:
   a) a track integrally formed onto the bottom portion of said perforated animal face; and
   b) a rail affixed onto a neck segment of said flat cloth body, whereby said rail can be inserted into said track to hold said flat cloth body under said perforated animal face.

20. A pediatric nebulizer enhancer as recited in claim 18, wherein said attaching means, further includes:
   a) a first VELCRO strip affixed onto the bottom portion of said perforated animal face; and
   b) a second VELCRO strip affixed onto a neck segment of said flat cloth body, whereby said second VELCRO strip can mate with said first VELCRO strip to hold said flat cloth body under said perforated animal face.

21. A pediatric nebulizer enhancer as recited in claim 18, wherein said perforated animal face is of a pig.

22. A pediatric nebulizer enhancer as recited in claim 18, wherein said perforated animal face is of a cow.

23. A pediatric nebulizer enhancer as recited in claim 18, wherein said perforated animal face is of a lion.

24. A pediatric nebulizer enhancer as recited in claim 18, wherein said perforated animal face is of an elephant.

25. A pediatric nebulizer enhancer as recited in claim 18, wherein said perforated animal face is of a bear.

26. A pediatric nebulizer enhancer as recited in claim 18, wherein said perforated animal face is of a lamb.

27. A pediatric nebulizer enhancer as recited in claim 18, wherein said perforated animal face is of a dog.

\* \* \* \* \*